United States Patent [19]
Kelly

[11] Patent Number: 4,746,571
[45] Date of Patent: May 24, 1988

[54] X-RAY DETECTOR EFFICIENCY STANDARD FOR ELECTRON MICROSCOPES

[75] Inventor: Thomas F. Kelly, Madison, Wis.

[73] Assignee: Wisconsin Alumni Research Foundation, Madison, Wis.

[21] Appl. No.: 893,044

[22] Filed: Aug. 1, 1986

[51] Int. Cl.$^4$ .................... B32B 9/00; G01N 23/00; G21K 7/00; H01K 1/08
[52] U.S. Cl. .................................. 428/328; 250/306; 250/310; 250/311; 250/399; 428/138; 428/913
[58] Field of Search ............... 250/310, 306, 399, 311; 428/328

[56] References Cited

PUBLICATIONS

N. J. Zaluzec, "Quantitative X-ray Microanalysis: Instrumental Considerations and Applications to Materials Science", Chapter 4 in *Introduction to Analytical Electron Microscopy*, Plenum Press, New York, 1979, 121-167.
W. E. King, "An Emperical Technique to Measure X-Ray Production and Detection Efficiencies in the Analytical Electron Microscopy"; *Symposium on High-Resolution Electron Microscopy*, Tempe, Ariz., Jan. 7-11, 1985.

*Primary Examiner*—George F. Lesmes
*Assistant Examiner*—D. R. Zirker
*Attorney, Agent, or Firm*—Isaksen, Lathrop, Esch, Hart & Clark

[57] ABSTRACT

An X-ray detector efficiency standard is formed of multiple spherical particles of various materials distributed over the surface of a substrate. The particles are preferably formed of pure materials, such as pure elements and stoichiometric compounds, having characteristic X-ray emission energies which span a range sufficient to determine the efficiency of the X-ray detector substantially over its operating range. The spherical particles may be formed by an electrohydrodynamic spraying process and have a diameter preferably in the range of 10 nanometers to 1 micron.

15 Claims, 3 Drawing Sheets

X-RAY DETECTOR EFFICIENCY STANDARD FOR ELECTRON MICROSCOPES

FIELD OF THE INVENTION

This invention pertains generally to the field of electron microscopy and related equipment, and particularly to X-ray detectors for electron microscopes and to the calibration of such detectors.

BACKGROUND ART

Energy dispersive X-ray analysis is frequently used to determine the composition of electron transparent specimens in electron beam instruments. Early techniques for determining composition included ratio techniques based on pure bulk samples and standard composition samples that could be used to convert X-ray intensities into elemental compositions. These approaches avoided the need to know in detail the X-ray detector efficiency, but consequently required standard samples for each element and accelerating voltage used. Pure, elemental thin film specimens have been used in a ratio technique to calibrate an X-ray detector for each element and operating voltage. These techniques and others in which the composition or determination is calculated from theoretical values without using standards have suffered from significant uncertainties associated with the X-ray detector. It has been proposed that the effects of the X-ray detector can be accounted for by determining a detector efficiency function (DEF) using standard alloy specimens. See, e.g., the article by N. J. Zaluzec in *Introduction to Analytical Electron Microscopy*, Plenum Press, New York (1979). The DEF is typically expressed as the relative X-ray detection efficiency of the X-ray detector as a function of X-ray photon energy. Once a DEF is determined for an instrument, the instrument is effectively calibrated for determining the composition of all elements and at all operating conditions. One approach proposed for determining the DEF is a technique using thin film specimens of pure materials to determine the detector efficiency at several discrete X-ray energies. See W. E. King; *Symposium on High-Resolution Electron Microscopy*, Tempe, AZ, Jan. 7–11, 1985.

The quantification of X-ray signals in electron microscopes to determine specimen composition requires the conversion of X-ray signal intensity from each element in a sample into a weight fraction for the sample. Because the efficiencies of production and detection of X-rays differ for each element in the sample, the ratio of signal intensities of two elements does not equal the ratio of their composition. For thin-film analysis, the ratio of intensities $I_a$ and $I_b$ for two elements (elements "a" and "b") can be related to the ratio of the composition of the elements, $C_a$ and $C_b$, by a constant, i.e., $C_a/C_b = K_{ab} I_a/I_b$, where $K_{ab}$ is experimentally determined. This equation forms the basis of the ratio technique for quantification of X-ray signals. To use this technique, $K_{ab}$ must be determined experimentally by the use of composition "standards". This approach, while quite reliable, is limited because alloy samples of known composition must be prepared for each element that is to be analyzed. It is sometimes difficult or impossible to prepare homogeneous samples for this purpose. Given the availability of suitable samples, the instrument must be calibrated for each element of interest. Furthermore, since the constant $K_{ab}$ is a function of the energy of the electrons, it must be determined for each accelerating voltage of the instrument.

Another approach to quantification handles the effects of X-ray production and X-ray detection separately. In this approach, the basis of quantification is the equation: $C_a/C_b = K_b \epsilon_b I_a / K_a \epsilon_a I_b$, where $K_a$ and $K_b$ are the X-ray generation constants for elements a and b and $\epsilon_a$ and $\epsilon_b$ is the efficiency of detection for X-ray photons from elements a and b. Because of its greater generality, this latter formulation of the ratio has been recognized as a preferable approach to quantification. The X-ray generation constants are dependent on the sample and the accelerating voltage and are reasonably well-known. However, it is difficult to be able to determine the efficiency of detection $\epsilon_a$ and $\epsilon_b$ for all elements. The theoretical form of the X-ray detector efficiency function is known, and thus a continuous detector efficiency function (DEF) could possibly be used, which would allow calculation of the values of the detector efficiency at the X-ray photon energies characteristically emitted by the elements a and b. However, because of the large uncertainties in some of the important parameters in this theoretical function (primarily with regard to the detector window thickness and dead layer thickness), outright theoretical calculation of the detector efficiencies $\epsilon_a$ and $\epsilon_b$ does not appear to be a satisfactory approach.

Several experimental techniques have been devised to determine the detector efficiency function, but these techniques have not found routine application. For example, experimental determinations of the detector efficiency at a particular X-ray energy can be made on samples of known composition. If pure materials are used as samples (elements or stoichiometric compounds), then any uncertainties in the nature of the composition are eliminated. However, the electron path length through the material must be known accurately to obtain accurate efficiency values. For thin foils used as samples in the transmission electron microscope, several samples of various materials must be made and examined in the microscope, and the sample thickness must be measured with accuracy for each sample. The time consuming and difficult task of analyzing several samples to obtain a one time calibration for any one instrument has been an impediment to the routine determination of detector efficiency functions.

SUMMARY OF THE INVENTION

An X-ray efficiency standard in accordance with the present invention may be utilized to calibrate the X-ray detectors of electron microscopes, or other electron beam instruments, by directing a beam of electrons at the standard to provide characteristic X-ray emission at selected energies. The output signal from the detector at each X-ray energy can be used to calculate the efficiency of the detector, and data from the detector at several energies over the operating range of the detector can be used to determine a best fit efficiency function for the detector.

The standard has plural substantially spherical particles distributed on a substrate, the particles preferably being formed of either pure elements or stoichiometric compounds of known composition, with the particles preferably having a diameter small enough to be electron transparent and minimize absorption and fluorescence effects, typically less than approximately 1 micron ($10^{-6}$ meter) The spherical particles may be formed of a variety of different elements which span a desired range of X-ray energies emitted from interaction of an electron beam with the particles. By focusing the electron beam on a selected sphere of a selected known pure element or stoichiometric compound, the operator of the microscope can determine the efficiency of the X-ray detector with respect to the characteristic energy X-rays emitted from that known element or compound.

Because the spherical particles of the efficiency standard are small spheres of pure materials, several advantages are obtained. First, the electron path length can be readily determined from the electron microscope image of the sphere, allowing the diameter of the sphere to be measured and the path length calculated. Secondly, many particles formed of a variety of elements can be deposited on a single substrate. Thus, a calibration over the entire desired X-ray energy range can be performed with a single standard which carries spheres of all elements of interest. Preferably, the standard includes several spherical particles formed of each of the materials, allowing the operator to choose the best sphere of a particular material for the calibration determination that he wishes to perform. The operator can choose to analyze spheres that are small enough that absorption and fluorescence corrections are small and may be neglected. Because of the spherical geometry of the target particles, if corrections are required for these factors, the corrections are much less severe than the corrections required for thin foil targets. Furthermore, tilting of the plane of the standard with respect to the electron beam does not affect the geometry of the spherical particles relative to the detector, so that there is neither a need for tilting the standard with respect to the detector, as in thin foil targets, nor any requirement for correction if the substrate of the standard is tilted.

The elements or stoichiometric compounds of which the spherical particles are composed are preferably selected such that the energy of the characteristic X-rays emitted from the various particles will cover the range of the X-ray detector. Generally, a standard which has spherical particles formed of about ten different elements is sufficient to obtain a reasonable measure of the detector efficiency function.

The standard of the invention may be produced by electrohydrodynamic spraying to produce small droplets of material which are deposited onto a temporary carrier, such as a layer of salt or a dissolvable polymer. A permanent substrate layer of material, such as carbon, may then be deposited over these spheres and a backing grid laid on the substrate layer to provide mechanical support. The temporary carrier may then be removed by, for example, dissolving it. The electrohydrodynamic process is particularly adapted to the formation of submicron spheres of material, yielding highly spherical geometries in the desired size range.

Further objects, features, and advantages of the invention will be apparent from the following detailed description when taken in conjunction with the accompanying drawings.

DESCRIPTION OF THE PREFERRED EMBODIMENT

Figure 1:
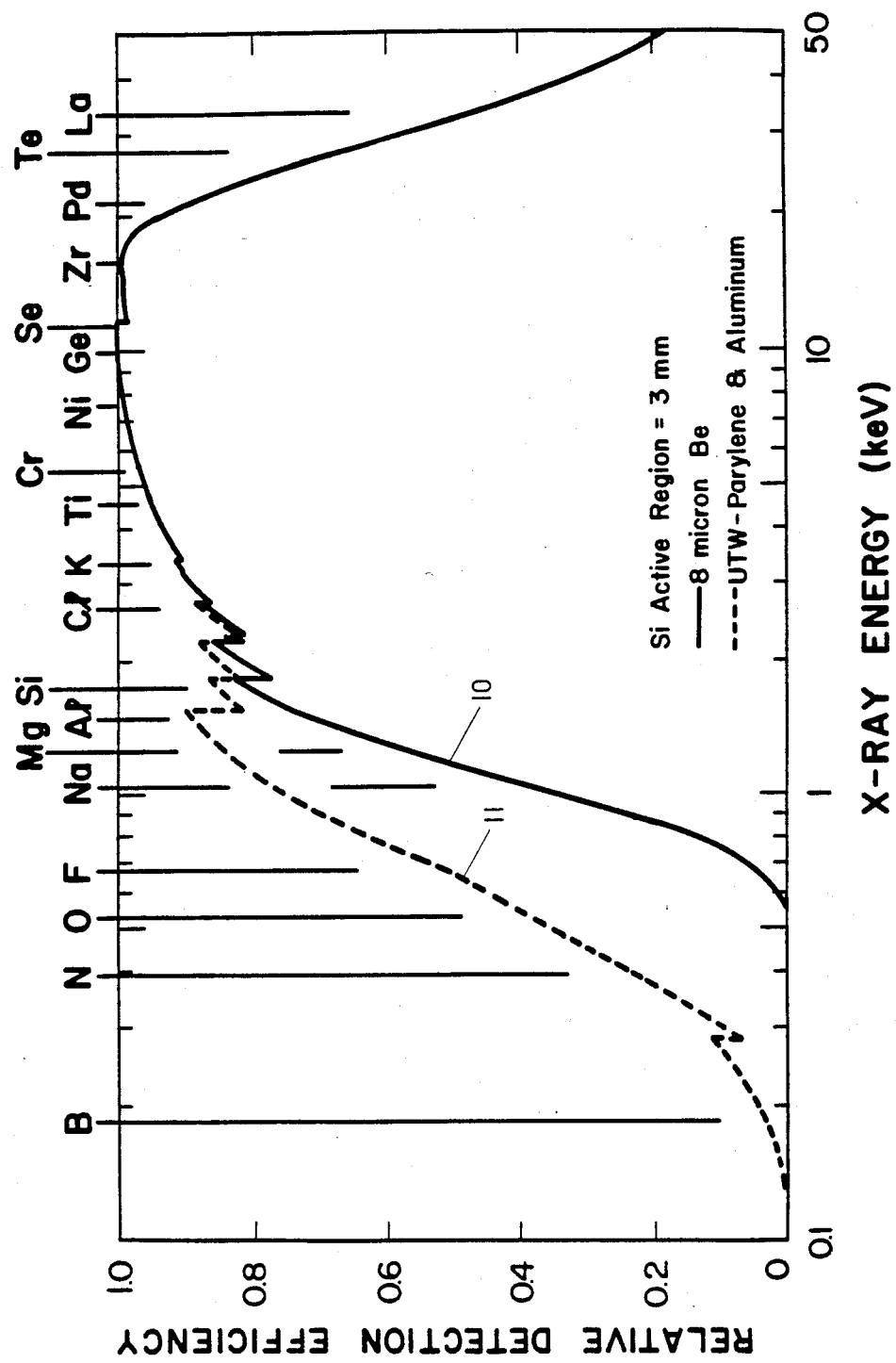
FIG. 1 is a calculated typical detector efficiency function with the characteristic energies of K-alpha emissions of various elements marked for illustration.

A particular advantage of the present invention is the ready calculation of the efficiency of an electron microscope X-ray detector over a relatively broad range of photon energies. The basis for the calculation of detector efficiencies may be illustrated by considering the ionization of the J-shell of an atom and emission of the characteristic photon at wavelength $\lambda$. It can be shown that the number N of photons detected by the X-ray detector for an element "a" in an alloy has the form:

$$N = A \cdot L \cdot K \cdot C_a \cdot \rho \cdot \delta \cdot \tau \cdot \epsilon$$

where A is Avogadro's number, L is the sum total distance traveled through the alloy by all high energy electrons incident upon the alloy in the electron microscope, $C_a$ is the weight fraction of the particular element a in the alloy, K is the X-ray generation constant for element a at wavelength $\lambda$, $\rho$ is the density of the alloy, $\delta$ is the absorption correction at wavelength $\lambda$ for element a, $\tau$ is the fluorescence correction at wavelength $\lambda$ for element a, and $\epsilon$ is the detection efficiency at wavelength $\lambda$. This expression can be solved for $\epsilon$ to yield the detection efficiency as follows:

$$\epsilon = \frac{N}{A \cdot L \cdot K \cdot C_a \cdot \rho \cdot \delta \cdot \tau}$$

In considering the foregoing expression, it is noted that the number N of photons detected is experimentally measured. Avogadro's number is a well-known constant and the density $\rho$ of the material containing element a can be known or measured accurately. The X-ray generation constant K can be determined from experimental data that have been assessed and tabulated. Although the best analytic formulation for the variation of the ionization cross section with electron energy and atomic numbers is still the subject of research, the experimental measurements are in relatively good agreement with models. The correction for the absorption $\delta$ have been derived for targets consisting of an infinitely wide, plain parallel sample, and corrections have been derived for spherical targets, although analytic solutions may not be available and numerical approximations must be used. However, generally, the corrections are much less significant for spherical targets than for thin foils, primarily because the absorption path length is limited by the finite size of the sphere. For pure elements, the corrections are even less significant. A given electronic shell of an element cannot be fluoresced by photons from relaxation events of the same shell. Thus, the fluorescence correction for a pure element is not needed (i.e., $\tau = 1$). In addition, the characteristic photons of interest can only be absorbed by transitions in lower energy shells in the same atom. The mass absorption coefficient of an element for its own characteristic radiation is therefore very low and the absorption correction for pure-element spheres is generally negligible for samples that are substantially "electron transparent". For an isolated sphere on a support film, each of these corrections is quite small compared to the corrections required for a thin film target.

The composition of a sample to be used as a standard for X-ray analysis is a significant factor. As long as the fraction $C_a$ is well-known, then it can be used for calibration. If an alloy is used as a standard, there is, however, always the question of whether the actual composition has been altered by preparation processes. The composition of a pure element eliminates this question ($C_a=1$). In addition, the composition of stoichiometric compounds is not generally subject to change during preparation processes. Many compounds hold stoichiometry to better than one part in a thousand. Compounds have the advantage in a standard that two or more elements are present in a single target. However, if compounds are used as targets, then absorption and fluorescence corrections may become necessary.

Finally, the electron path length L must be known accurately. In prior X-ray detector calibration techniques, where a thin foil of a particular material is used as the standard, the thickness of the foil must be measured accurately, a difficult requirement for very thin foils. It is possible to obtain highly accurate thickness measurements (within a few percent) using convergent beam electron diffraction techniques on metal foils, but this is a tedious procedure of limited applicability. In contrast, the diameter of a particular spherical particle used as a standard electron beam target can be determined from its electron micrograph image, and knowledge of the diameter allows the electron path length to be readily calculated based on the simple geometry of the sphere.

The path length L can be readily determined for the various electron beam configurations that occur in both transmission electron microscopes and scanning electron microscopes. For example, assuming that the electrons penetrate the sample, i.e., the spheres are electron transparent, the simplest electron path calculation is for a stationary point probe. The total electron path length L is simply the product of the number of electrons (the integral of the beam current in time) and the path length of each electron:

$$L = P I_b T/e,$$

where $$P = (D_s^2 - 4r^2)^{\frac{1}{2}},$$

and where $D_s$ is the measured diameter of the sphere, r is the radial distance from the center of the sphere to the line on which the electron beam passes through the sphere, T is the total time of application of the electron beam, $I_b$ is the beam current, and e is the charge per electron. Such a stationary probe example would be most applicable to a scanning transmission electron microscope or a scanning electron microscope.

For a more complex case where a target sphere is inside the bounds of the raster of a scanned point probe, it can be shown that the total electron path length L for a number F of frames is then: $L = F\, L_f$, where $$L_f = 4 \sum_1^{N_s} L_n, \text{ and } L_n = D_s(I_b/2e)(t_1/S_1) \cdot [S_{sn}(1 - S_{sn}^2)^{\frac{1}{2}} + \arcsin(S_{sn}) - S_{on}(1 - S_{on}^2)^{\frac{1}{2}} + \arcsin(S_{on})],$$

where $S_1$ is a dimensionless scan length at time $t_1$, $t_1$ is the scan time per line, $S_{on} = n S_1$, $S_{sn} = (n + D_{mn}/2W) \cdot S_1$, $D_{mn}$ is the minor diameter of the nth line in the scan, and W is the scan width. The number $N_s$ is determined in accordance with the expression:

$$N_s = (D_s/2h) \cdot (t_f/t_1),$$

a number indicating the number of scan lines that intercept one quadrant of the sphere, and $t_f$ is the scan time per frame and h is the height of the scan.

A third type of beam interaction with a specimen is that of a flooding beam such as provided in a transmission electron microscope. Assuming a uniform current density in the beam which illuminates an area having a diameter $D_i$, then the integrated electron path length becomes:

$$L = \tfrac{2}{3}\, (I_b t/e)\, (D_s^3/D_i^2),$$

where $I_b$ is the beam current, t is the counting time, e is the electron charge, $D_s$ is the measured sphere diameter, and $D_i$ is the diameter of the area illuminated by the electron beam.

The absolute detector efficiency function can be shown in theory to have the form of the product of exponential functions of the mass absorption coefficients and layer thicknesses of the various materials forming the detector, i.e., the detector window, the gold front electrical contact, the silicon dead layer, and the silicon active layer. See e.g., N. J. Zaluzec, EMSA Bulletin, Spring 1984, Vol. 14, No. 1, pp. 67–75; EMSA Bulletin, Fall 1984, Vol. 14, No. 2, pp. 61–72. As noted above, by utilizing a standard in accordance with the present invention to measure N and L experimentally at a particular photon energy, then the value of the detector efficiency function may be determined at that corresponding energy. By determining the value of $\epsilon$ at several energies using several different target materials, a detector efficiency function may be fit to the experimental data through the individual data points. For example, a least squares fit to the experimental data may be obtained by varying adjustable parameters, namely the thicknesses of the absorbing layers. See N. J. Zaluzec in *Introduction to Analytical Electron Microscopy*, Plenum Press, New York (1979). Such a fitting procedure will give a function that can thereafter be used to calculate the detector efficiency at any energy in its range. Examples of such relative detection efficiency functions are shown by the graphs 10 and 11 in FIG. 1, with the energy of K-alpha emissions of various elements noted with respect to these graphs.

Certain factors affecting the detection efficiency function are prone to change over time. For example, a film of oil from the oil pump vacuum system may condense on the detector window, carbon contamination layers may form on the sample, and ice may condense on the detector crystal due to imperfections in the detector vacuum system. Consequently, it is helpful to be able to determine the detector efficiency function routinely and easily so that the function can be determined as frequently as desired by the operator. These objectives are efficiently accomplished utilizing the X-ray detector efficiency standards produced in accordance with the present invention.

Figure 2:
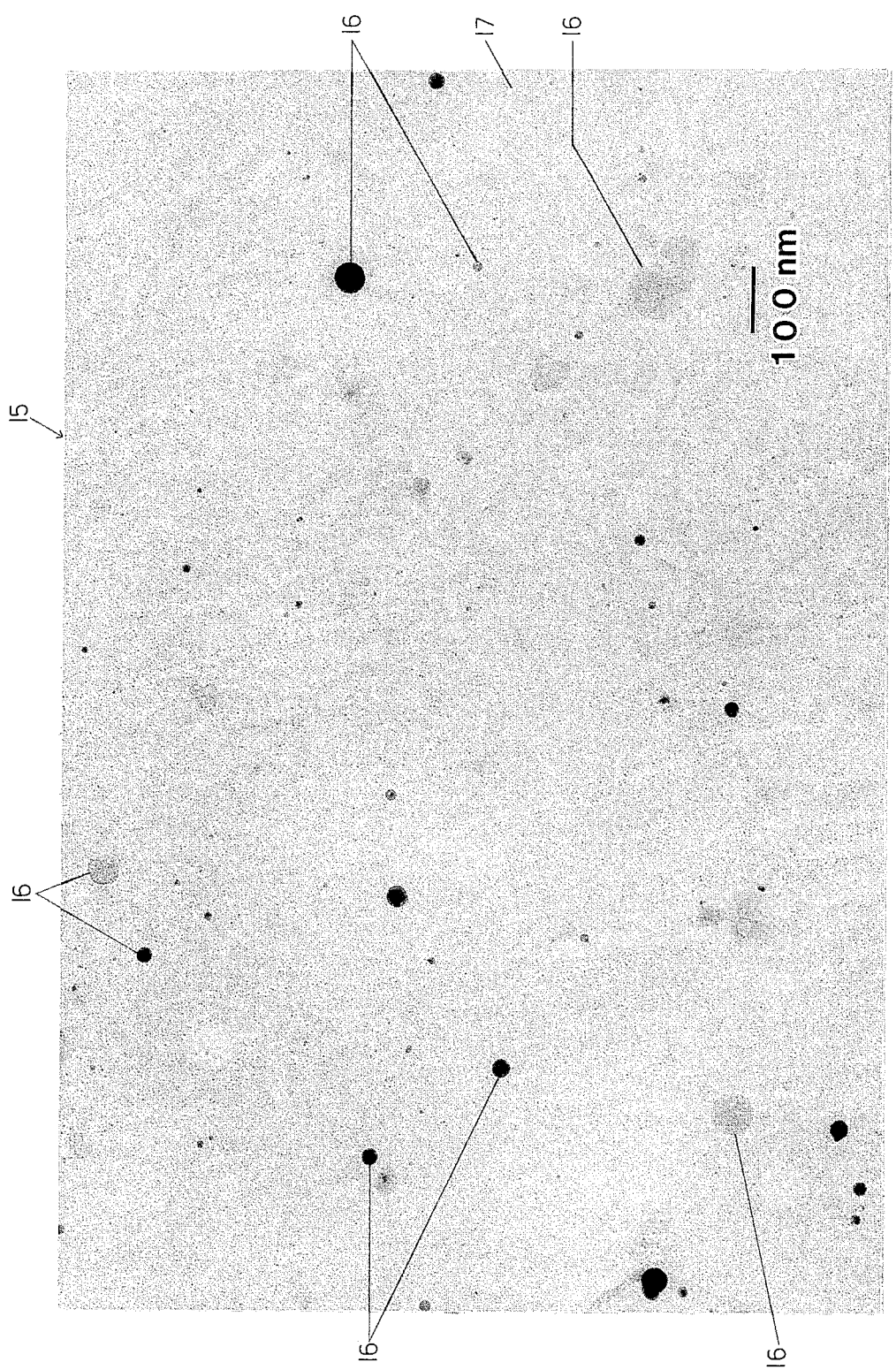
FIG. 2 is a transmission electron micrograph of an X-ray detector efficiency standard of the invention.

FIG. 2 shows a transmission electron micrograph (at a magnification of approximately 120,000 X) of an X-ray detector efficiency standard 15 which has a number of target spheres 16 of various sizes distributed over and carried upon the surface of a substrate layer 17 formed of a carbon film. The photomicrograph is calibrated and a distance equivalent to 100 nanometers is illustrated on the photomicrograph. Each of the spheres 16 is formed of a material, such as a pure element or a stoichiometric compound, which will yield characteristic emitted X-ray photons of known energy in response to incident electrons. It is preferred that numerous spheres of various different materials be distributed about the surface of the standard 15 so that the operator can move from one sphere, formed of one material, to another sphere formed of another material and so on to obtain measurements at several X-ray energy points, for example 10 or more, over the operating range of the X-ray detector. These materials may include pure metallic elements (for example, good results may be obtained with aluminum, copper, palladium, vanadium and many others) and stoichiometric compounds (e.g., alumina).

From a calibrated micrograph, such as that shown in FIG. 2, the operator can readily determine the diameter of a selected target sphere and thereby calculate the electron path length L for the particular type of electron beam illumination which will be used for the calibration measurements. The operator can scan over the surface of the standard 15 until he finds a spherical particle 16 of the size and material which he wishes to utilize for a calibration measurement, and then may proceed to take measurements at that sphere. Since all the spheres on the standard will be apparent to the operator and can be visually inspected by him using the electron microscope prior to calibration measurements being made, the operator can choose well-formed spherical particles as targets so that the electron path length L can be accurately determined from the diameter of the particle. The spherical particles are preferably of a size which, for the material of the particle, allows the particle to be electron transparent and results in negligible fluorescence or absorption effects. Satisfactory electron transparency is generally obtained if 50% or more of the electrons can pass through the particle without inelastic collisions. Although the desired particle sizes will vary with material, it is generally preferred that the average diameter of the particles is less than 1 micron. For most materials, the desired particle diameters will be substantially less than a micron, as the absorption and fluorescence effects are reduced and transparency increased as particle diameter decreases. However, the particles selected as targets should be well formed spheres to ensure that the electron pathlength can be accurately determined from a measurement of the diameter of the sphere. In addition, the sphere must be sufficiently large (e.g., generally greater than 10 nanometers) that the resolution of the microscope allows the operator to determine the particle diameter to high accuracy, preferably to within 1%. The particles 16 are distributed randomly about the substrate 17, as illustrated in FIG. 2, with most of the particles being sufficiently far apart—e.g., several diameters distance from one another—that it is possible for the operator to focus on a single particle.

Figure 3:
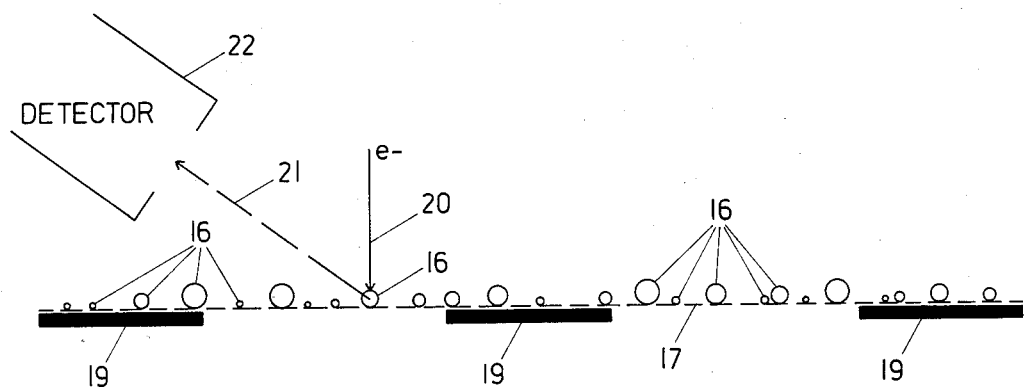
FIG. 3 is a simplified side view of the X-ray detection efficiency standard, illustrating the path of an electron with respect to a particular spherical particle and the X-ray emitted therefrom.

For use in transmission electron microscopes, the substrate layer 17 on which the particles 16 are supported is preferably relatively thin compared to the diameter of the particles 16 so it is essentially electron transparent and formed of a material, preferably of lower atomic weight, which has a characteristic X-ray emission which is significantly distinct from the X-ray photon energies emitted from the target spheres. An example of a suitable material for the layer 17 is a carbon film of 10 to 50 nanometer thickness supported on a wire mesh grid 19 which provides mechanical support, as illustrated in FIG. 3, in which solid portions of the wires of the grid 19 are shown. Ideally, the electron beam 20 would impinge on a particular spherical particle 16 which was positioned in the space between the wires of the mesh 19 so that the X-ray beam 21 which strikes the X-ray detector 22 would be composed of X-ray photons emitted from the target spherical particle 16 and not from the wire of the grid 19.

Figure 4:
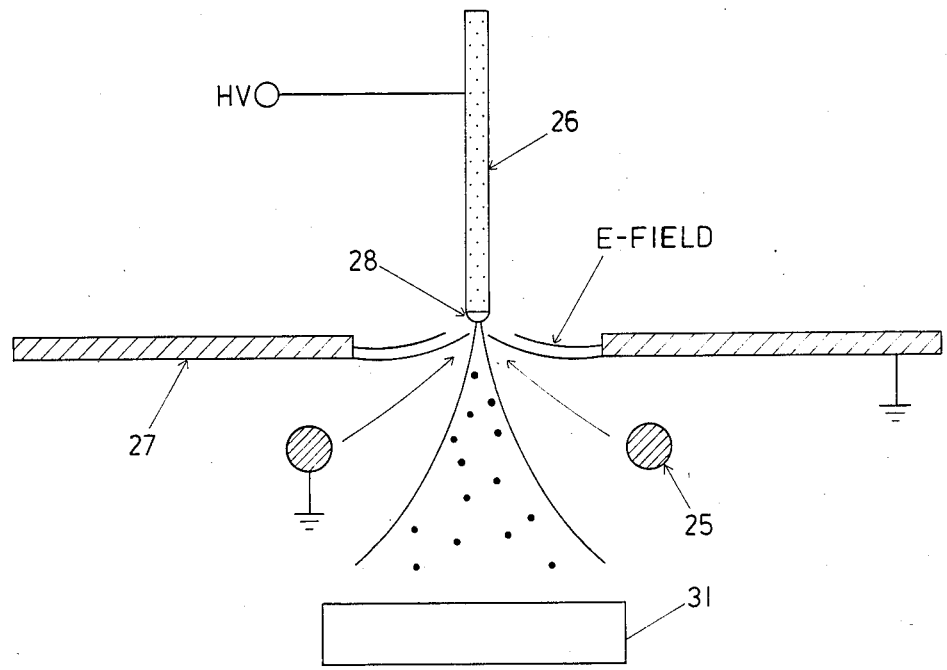
FIG. 4 is a diagrammatic view illustrating the electrohydrodynamic deposition of spherical particles on a temporary carrier.

A suitable process for forming submicron diameter spherical particles is the electrohydrodynamic spraying process, generally described in U.S. Pat. No. 4,264,641, and carried out by equipment available from Phrasor Technology, Inc., of Duarte, Calif. as schematically illustrated in FIG. 4. An annular thermionic emitter electron source 25 emits electrons which strike and heat the tip of a consummable electrode wire 26 formed of the material frOm which the spherical particles are to be formed and biased to a high positive voltage. An opposing extraction cathode 27 is held at about 20 Kv relative to the wire 26 and the resulting electric field causes the molten tip 28 of the wire 26 to be pulled into a spike which breaks free from the wire and sprays out in small droplets. The droplets leave with a residual charge and are therefore accelerated by the field. This droplet generating system is enclosed in a vacuum chamber. Because of the very high surface area to volume ratio of these very small droplets, they cool radiatively at about $10^6$ K per second and solidify rapidly in free flight to form a droplet beam 29 of spherical particles. In principle, any material that can be made into a thin diameter wire ($\frac{1}{2}$ mm diameter or smaller) and that will support the electric current necessary to melt the material can be used to form the particulate spray in this manner. It is even possible to spray certain ceramic materials by shrouding them with an electrical conductor or using tubes with a metal wire in the center. Once at high temperatures, the ceramic materials will generally support the small electron beam current required to heat them.

To form the structure of the standard, the droplets 29 may initially be sprayed onto a dissolvable carrier 31, for example, formed of crystalline salt (NaCl) or a dissolvable polymer. As an example, wires of pure palladium, vanadium and copper and rods of alumina were sprayed onto a carrier 31 formed of crystalline sodium chloride which was placed at about 0.5 meter from the source of the droplet beam 29. After spherical particles of each of the materials were sprayed in turn onto the substrate, a very thin film of carbon was sublimated on top of the solidified particles to serve as the substrate film 17. The carbon film with spheres attached was floated off the carrier in distilled water which dissolved the sodium chloride carrier. Standard copper mesh sample grids were used to support the isolated carbon films. The wire mesh composition should preferably not contain any of the elements that are to be analyzed on the standard. The wire mesh grid 19 serves to physically support the carbon substrate film and the spherical particles distributed thereon.

As discussed above, to determine the absolute detector efficiency, it is necessary that the electron path length L be known accurately. This means that it is necessary to have accurate knowledge of the actual beam current and target sphere diameter. In general, a Faraday cage may be used to obtain accurate measurements of the beam current. To know the absolute sphere diameter, it is necessary that the magnification of the electron microscope be calibrated so that accurate absolute sphere diameters may be obtained. However, where relative detector efficiencies are to be determined, the foregoing conditions are not required. All that is required is that the beam current be maintained constant.

The most significant advantage of utilizing the standard of the present invention is convenience for the operator. The electron path length L is readily determined, the compositions of the spherical targets are known and certain, a detector can be calibrated over a series of elements using a single standard so that the operator need not change samples in the microscope, absorption by the spheres is low and even relatively large spheres are effectively "thin" targets, and fluorescence correction is not needed for spherical particles formed of pure elements. In composition measurement, this allows universal calibration of the electron microscope X-ray detector and provides an experimental basis for composition measurements. Because use of such standards allows simple and reliable calibration of a detector, the likelihood of frequent use is much greater than with present standards. With appropriate software control of the electron microscope, the calibration process may be automated for a standard set of elements.

Some X-ray detectors have the option of switching between two windows or even changing windows. By measuring the detector effiency at any energy where there is a significant difference in the absorption of the two windows, the thickness of each window can be determined.

The electrohydrodynamic process is particularly advantageous for producing standards in accordance with the invention since standards can be made in relatively large quantities with substantially no significant variation from sample to sample. The spherical particles on the standards can be composed of many different elements by spraying the sample elements onto a substrate one at a time, and the samples are processed in a clean vacuum environment.

Any measured quantity associated with X-ray analysis can potentially benefit from the relatively high accuracy of measurements made on small diameter spheres. For example, if the efficiency function of a particular detector is well-characterized (using the technique of the present invention), then it is possible to measure the ionization cross-section of materials using such spherical particles. If the X-ray detector efficiency is known, then the ionization cross-section may be determined in accordance with the equations given above. The fluorescence yield, radiative partition ratio, and atomic weight are relatively well-known compared to the ionization cross-section. Thus, submicron spherical particle targets formed in accordance with the present invention may be utilized for careful measurements of cross-sections of a variety of elements that can be sprayed into spheres by the above described electrohydrodynamic process.

Another application of the spherical particle targets of the present invention is in the measurement of effects associated with incomplete charge collection in the silicon-lithium detector. Since the number of X-rays that should be detected is well-known, any discrepancies can be attributed to incomplete charge collection.

It has been proposed that electron energy loss spectroscopy (EELS) can be used to measure thicknesses of specimens from the ratio of the inelastic to elastic scattered electron intensities. Spherical particles formed of pure materials in accordance with the present invention provide ideal targets on which to perform such tests. Since electrons will pass through the support film 17, it will be necessary to deconvolute the effects of the film on the EELS spectra.

It is understood that the invention is not confined to the particular structures and techniques herein illustrated and described, but embraces such modified forms thereof as come within the scope of the following claims.

What is claimed is:

1. An X-ray detector efficiency standard for electron microscopes, comprising:
   (a) a substrate layer;
   (b) a plurality of substantially spherical particles in an amount sufficient to calibrate the X-ray detector, wherein each of the particles has a diameter sufficient to determine the length of an electron path, wherein the particles are distributed on the substrate, the particles formed of pure elements or stoichiometric compounds of known composition which yield characteristic emitted X-ray photons of known energy in response to incident electrons and having diameters such that the effects of fluorescence and absorption in the spherical particles on X-rays emitted as a result of electron beam interaction with the spherical particles is negligible, and the particles are substantially electron transparent.

2. The standard of claim 1 wherein a portion of the plurality of substantially spherical particles distributed on the substrate have diameters less than 1 micron.

3. The standard of claim 2 wherein the average diameter of the spherical particles is less than 1 micron.

4. The standard of claim 1 wherein the substrate is formed of a layer of carbon sufficiently thin to be essentially electron-transparent, wherein the layer of carbon is supported by a metal mesh grid.

5. The standard of claim 2 wherein the plurality of substantially spherical particles distributed on the substrate include substantially spherical particles formed of different pure elements and stoichiometric compounds and wherein the plurality of substantially spherical particles have diamaeters in the range from 10 nanometers to 1 micron.

6. The standard of claim 1 wherein the spherical particles distributed on the substrate are formed of a sufficient number of different elements which have different characteristic X-ray emission energies to cover substantially the operating range of a selected electron microscope X-ray detector.

7. The standard of claim 1 wherein there is at least one substantially spherical particle distributed on the substrate in a diameter range of 10 nanometers to 1 micron which is formed of one of at least ten different elements whose characteristic X-ray emission energies are different from one another.

8. The standard of claim 1 wherein the spherical particles are formed by electrohydrodynamic spraying.

9. The standard of claim 1 which exhibits an X-ray detector efficiency illustrated in a transmission electron micrograph as shown in FIG. 2.

10. The standard of claim 1 wherein the spherical particles distributed on the substrate include plural spherical particles from the group consisting of aluminum, palladium, vanadium, copper, and alumina.

11. An X-ray detector efficiency standard for electron microscopes, comprising:
    (a) a substrate layer;
    (b) a plurality of substantially spherical particles of known composition which yield characteristic emitted X-ray photons of known energy in response to incident electrons distributed on the substrate, the particles having an average diameter less than 1 micron such that the effects of fluorescence and absorption in the spherical particles on X-rays emited as a result of electron beam interaction with the spherical particles is negligible.

12. The standard of claim 11 wherein each spherical particle is formed of either a pure element or a stoichiometric compound of known composition which yields characteristic emitted X-ray photons of known energy in response to incident electrons, wherein there are spherical particles formed of at least two different pure elements or stoichiometric compounds, and wherein there are plural spherical particles of each selected element or stoichiometric compound.

13. The standard of claim 11 wherein the spherical particles are formed by electrohydrodynamic spraying.

14. The standard of claim 1 wherein the substrate layer is relatively thin compared to the diameter of the substantially spherical particles, essentially electron transparent, made of a material of low atomic weight, and has a characteristic X-ray emission which is significantly distinct from the X-ray photon energies emitted from the target spheres.

15. The standard of claim 1 wherein the substantially spherical particles are of a size sufficient to allow the particles to be electron transparent and result in negligible fluorescence or absorption effects.

* * * * *